United States Patent [19]

Hung et al.

[11] Patent Number: 4,734,362
[45] Date of Patent: Mar. 29, 1988

[54] PROCESS FOR PURIFYING RECOMBINANT PROTEINS, AND PRODUCTS THEREOF

[75] Inventors: Chung-Ho Hung; Richard Thorn, both of Milford; Charles Riggin, Hopdale; Dante Marciani, Hopkinton, all of Mass.

[73] Assignee: Cambridge Bioscience Corporation, Worcester, Mass.

[21] Appl. No.: 911,455

[22] Filed: Sep. 25, 1986

Related U.S. Application Data

[63] Continuation-in-part of Ser. No. 825,597, Feb. 3, 1986.

[51] Int. Cl.$^4$ ..................... C07K 3/00; G01N 33/546
[52] U.S. Cl. .......................................... 435/68; 435/5; 436/533; 436/534; 436/547; 530/412; 530/826
[58] Field of Search ..................... 435/5, 68; 436/533, 436/534, 547; 530/412, 826

[56] References Cited

U.S. PATENT DOCUMENTS

| | | |
|---|---|---|
| 4,021,303 | 5/1977 | Nakabayashi . |
| 4,168,262 | 9/1979 | Kinsella et al. . |
| 4,348,479 | 9/1982 | Kinsella et al. . |
| 4,427,580 | 1/1984 | Kinsella et al. . |
| 4,511,503 | 4/1985 | Olson et al. . |
| 4,512,922 | 4/1985 | Jones et al. . |
| 4,518,526 | 5/1985 | Olson et al. . |
| 4,520,113 | 5/1985 | Gallo et al. . |
| 4,551,502 | 4/1985 | Builder et al. . |
| 4,591,571 | 5/1986 | Kuboyama et al. . |
| 4,599,197 | 7/1986 | Wetzel . |
| 4,661,445 | 4/1987 | Saxinger et al. . |

OTHER PUBLICATIONS

*Chemical Abstracts*, vol. 104, No. 21, 184841v (May 26, 1986).
S. J. Tarnowski, "Practical Aspects in the Recovery of Proteins Produced by Recombinant DNA Technology," *Pharmaceutical Technology*, pp. 70-72, 79 (1983).
Atassi et al., *Methods in Enzymology*, 49:546-553 (1972).
Eshhar et al., *Eur. J. Immunol.*, 1:323-329 (1971).
Shetty et al., *Biochem. J.*. 191:269-272 (1980).
Brinegar et al., *J. Agric. Food Chem.*, 28:818-824 (1980).
Shetty et al., *J. Agric. Food Chem.*, 30:1166-1171 (1982).
Lundahl et al., *Biochem. biophys. Acta.*, 379:304-316 (1975).
Brinegar et al., *Int'nl. J. Peptide Protein Res.*, 18:18-25 (1981).
Light, *Biotechniques*, 3:298-308 (1985).
Snyder et al., *Carbohydrate Res.*, 105: 87-93 (1982).

*Primary Examiner*—Sidney Marantz
*Attorney, Agent, or Firm*—Saidman, Sterne, Kessler & Goldstein

[57] ABSTRACT

The present invention relates to a process for recovering recombinant protein from refractile inclusion bodies of microorganisms which comprise disrupting cells, recovering refractile bodies containing recombinant protein, solubilizing the refractile bodies with a denaturant, protecting sulfhydryl groups of recombinant proteins, converting cationic amino groups of recombinant proteins to anionic carboxylic acid by derivatization with organic cyclic acid anhydrides, and recovering recombinant protein derivatives.

The present invention also relates to the production of solid supports coated with recombinant protein recovered by the process of the invention, and the use of said devices for the detection and quantification of antibodies to said recombinant proteins in body fluids.

37 Claims, 9 Drawing Figures

PROCESS FOR PURIFYING RECOMBINANT PROTEINS, AND PRODUCTS THEREOF

This application is a continuation-in-part of application Ser. No. 825,597, filed Feb. 3, 1986.

BACKGROUND OF THE INVENTION

1. Field of the Invention

This invention is directed to a process for isolating, from microbial refractile inclusion bodies, recombinant proteins and polypeptides that are difficult to solubilize and separate by previously known techniques. The process involves disruption of the microbial biomass, collection of refractile bodies, and solubilization of refractile body protein. Solubilization is effected by a combination of physical, chemical, and enzymatic means, with protection of free sulfhydryl groups of the recombinant protein by use of reversible of irreversible blocking agents. The free amino groups of proteins are then derivatized by reaction with cyclic acid anhydrides and individual protein derivatives separated using molecular sieves and ion exchange chromatography. The sulfhydryl and amino groups of the separated proteins are then deblocked.

Included in the invention is the preparation of diagnostic devices comprising solid supports coated with the separated recombinant protein antigens, and the use of the diagnostic devices for assays of antibodies in body fluids.

2. Brief Description of the Background Information

Recombinant DNA technology has permitted the expression of foreign (heterologous) proteins in microbial and other host cells. In many instances, high expression of recombinant proteins leads to the formation of high molecular weight aggregates, often referred to as "inclusion bodies" or "refractile bodies" (Old and Primrose, *Principles of Gene Manipulation*, Third Edition, Blackwell Scientific Publishers, Oxford, 1985, pp. 289–290). The inclusion bodies fall into two categories: first, paracrystalline arrays in which the protein presumably is in a stable conformation, although not necessarily native; and second, amorphous aggregates that contain partially and completely denatured proteins, as well as aberrant proteins synthesized as a result of inaccurate translation. Such aggregates of heterologous protein constitute a significant portion of the total cell protein.

Although inclusion bodies probably afford protection to proteins against endogenous proteases, they do present problems of extraction and purification, as they are very difficultly soluble in aqueous buffers. In most instances, denaturants and detergents (e.g., guanidine hydrochloride, urea, sodium dodecylsulfate (SDS), Triton X-100) have to be used to extract the protein. For proteins of pharmaceutical interest, particularly for parenteral administration, the use of detergents and denaturants is undesirable because it is difficult to remove them completely from isolated proteins, particularly if the proteins possess extensive hydrophobic domains. Further, if guanidine hydrochloride (guanidine.HCl), a strong denaturant, is employed, renaturation of the isolated proteins may be difficult, if not impossible, and the resultant heterologous proteins may be biologically inactive due to incorrect folding or conformation. In addition, if urea, a relatively weak denaturant, is used as the extractant, modification of some amino acid residues may occur.

Another problem in the recovery of the desired proteins which are in the form of refractile bodies is the need, not only to separate refractile proteins from other host cellular materials but also subsequently to remove refractile body protein contaminants from the desired refractile body heterologous protein. The second problem is probably due to the strong attraction that refractile body proteins have one for another, due perhaps to ionic attractions or hydrophobic bonding.

In a series of closely related patents (Builder, et al., U.S. Pat. Nos. 4,551,502; Olson, et al., 4,511,503; Jones, et al., 4,512,922; and Olson, 4,518,526), the inventors teach a process for converting *E. coli* refractile body recombinant proteins from the natural or induced insoluble state into soluble forms. The techniques use a combination of membrane disruption methods such as sonication or homogenization under high pressure, coupled to solubilization of proteins and strong denaturants such as guanidine.HCl and in ionic detergents such as SDS. After such treatments the recombinant proteins are refolded by buffer exchange into a relatively weak denaturant such as urea in the presence of a reducing agent such as 2-mercaptoethanol (buffer exchange may be preceded by sulfitolysis of proteins by contacting proteins with sulfite and a mild oxidizing reagent). The recombinant proteins are then isolated using ion exchange and molecular sieve chromatography in the presence of buffered urea. Thus, according to these patents, denaturants must necessarily be present throughout, and subsequent to, the process for recovering refractile body proteins.

Two patents from Kinsella et al. (U.S. Pat. Nos. 4,168,262 and 4,348,479) and two technical reports from the same group (Shetty et al., Biochemical Journal, 191:269–272 (1980); Shetty et al., Journal of Argricultural and Food Chemistry, 30:1166–1172 (1982)) teach a process of separating microbial proteins in bulk from nucleoprotein complexes. The process comprises disruption of the biomass by physical means in the absence of detergents of denaturating reagents. This is followed by centrifugation to remove cell debris, derivatization of the water-soluble proteinaceous material-nucleic acid mixture with an organic dicarboxylic acid anhydride such as citraconic or maleic anhydride, and subjecting the derivatized proteins (freed of insoluble cell debris by centrifugation) to isoelectric precipitation at pH 4.0–4.5. Next, the blocking N-acyl groups are removed by hydrolysis at acid pH, the protein solution is dialyzed to reomve salts, and the nucleic acid- depleted bulk proteins are isolated by lyophilization or isoelectric precipitation. It is important to note that the goal of the two Kinsella et al. patents and the Shetty et al. technical reports is to isolate bulk microbial proteins in a form suitable for human consumption. The purpose of the N-acylation step is to separate the desired bulk proteins from microbial nucleic acid contaminants.

Citraconylation has also been used to solubilize proteins from mammalian cells. Eshhar et al., *Europoean Journal of Immunology*, 1:323–329 (1971), reported that 60–70% of membrane proteins from rat thymocytes and lymphocytes were solubilized by citraconylation, and that these protein derivatives were antigenically inactive until decitraconylated at pH 5. Only 10–20% of the original antigenicity was recovered by deacylation. Lundahl et al., *Biochim. Biophys. Acta*, 379: 304–316 (1975), disclosed the use of citraconylation to solubilize a portion of water-insoluble human erythrocyte membrane proteins. Citraconylated proteins were further separated by SDS-polyacrylamide gel electrophoresis (SDS-PAGE) or on hydroxyapatite columns.

Kinsella et al., *International Journal of Peptide and Protein Research*, 18:18–25 (1981), disclosed that citraconylation of proteins is not limited to N-acylation of the primary amino groups of lysine residues. Citraconic anhydride also alkylates some free sulfhydryl groups, leading to cross-linking, and thereby aggregation, of proteins.

Light, *Biotechniques*, 3:298–308 (1985) disclosed that the solubility of unfolded proteins increases, and aggregation is avoided, when amino groups are derivatized with citraconic anhydride.

Snyder et al. *Carbohydrate Research*, 105:87–93 (1982) use citraconylation to solubilize human salivary proteins, and to dissociate mucin glycoproteins from extraneous proteins. No attempt was made to separate individual citraconylated proteins.

It would be useful to provide a method that solves the problems in solubilizing and separating microbial recombinant heterologous proteins by using procedures which, in their various aspects, succeed in solubilizing the proteins, removing contaminating host cellular proteins, and separating individual recombinant proteins in forms that are active and appropriate in biological and immunoassays, and that are soluble and biologically active in the absence of any denaturant or detergent.

SUMMARY OF THE INVENTION

The present invention is directed to a process for recovering, in active form, recombinant polypeptide or protein that have been produced in microbial cells, that is heterologous thereto, and that is, at least partially, deposited inside the cells within refractile inclusion bodies, i.e., clumps of insoluble protein. The present invention is also directed to the production of solid supports, coated with individual recombinant proteins recovered by the process of the invention, said coated solid supports being suitable for diagnostic assays of the solid state types.

The invention concerns a process for separating recombinant heterologous protein from background host cell protein through lysis of whole cells, followed by recovery of refractile bodies by any suitable method, such as by low speed centrifugation. The refractile body protein is dissolved in a surfactant/denaturant solution, the sulfhydryl groups are reversibly or irreversibly derivatized, thereby protecting such groups during subsequent manipulations of the protein; the derivatives are then fractionated.

Disaggregation of recombinant protein is effected by imposing on this protein a large negative charge, by converting cationic amino groups to anionic carboxylic acid groups. The doubly derivatized proteins may then be fractionated by chromatographic procedures, followed by restoration of the purified recombinant protein to an unblocked, renatured, biologically active form.

A different embodiment of the invention is concerned with producing solid supports coated with recombinant protein suitable, after deblocking, for a variety of diagnostic assays.

These aspects of the invention provide multi-step protocols that are applicable to insoluble heterologous recombinant proteins in host cell culture, regardless of their genetic source or biological nature, thus having the advantage of offering uniformity of chemicals and equipment requirements for any desired product.

The procedures are applicable generally, with only minor modifications or adjustments being required for a specific protein. The various aspects of this invention, by suitable combination and selection thereof, provide a solution to the problem of recovery of refractile body portein.

Briefly described, the scheme of FIG. 1 has several phases: In the first phase, the insoluble recombinant protein is liberated from the host cell by employing enzymatic and/or chemical means that disrupt the strong outer cell wall membrane under conditions of pH and ionic strength such that host cell proteins will be solubilized, or at least will remain in suspension at sedimentation forces sufficient to sediment recombinant protein-containing inclusion bodies. The enzymes and chemicals (detergents and weak denaturants) employed are those that are known to attack host cell walls and various macromolecular structures such as membranes and nucleoprotein bodies, thereby promoting cell lysis. Although the sedimented pellet contains predominantly the desired recombinant protein, it is also contaminated at this stage with small amounts of soluble host cell proteins that require removal.

In the second phase, contaminating host cell proteins are removed from the recombinant protein aggregates by washing with a mild solution containing both detergents and a weak denaturant.

As the recombinant protein has been precipitated in vivo under cytoplasmic conditions, it is clear that conventional aqeuous solubilization techniques will fail. Hence, in the third phase, a more drastic means is employed to bring the inclusion bodies into solution. It has been found that a strong denaturing solution is effective in doing this.

The strong denaturing reagent will also cause unfolding of the 3-dimensional structure of the desired recombinant protein, thereby exposing free sulfhydryl groups to air oxidation and other undesirable side effects. To obviate this difficulty, as well as to protect sulfhydryl groups from reacting with cyclic acid anhydrides in the fourth phase of the invention, described herein below, the invention provides, in this third phase, for the derivatization of the free sulfhydryl groups by various reagents. Sulfhydryl reagents, according to the invention, are either reversibly or irreversibly bonded to the free sulfhydryl groups.

A partial purification of the desired protein is achieved by desalting the sulfhydryl derivatization reaction mixture by dialysis or any other method under conditions wherein the desired protein precipitates out of solution as the concentration of denaturant is lowered by dialysis.

At this stage, recombinant and other contaminating proteins that had the host cells' inclusion bodies as their origin still have a tendency to aggregate in the absence of high concentrations of strong denaturants. However, proteins in the denatured condition do not exhibit their normal biological activities. Thus, an alternate means was sought to maintain the recombinant protein in solution in the absence of strong denaturants. This alternative, according to the fourth phase of the invention, comprises reacting free amino groups of the recombinant protein with selected cylic dicarboxylic acid anhydride compounds. This reaction produces a change in the overall charge of the recombinant protein, as its cationic amino groups are converted to anionic carboxylic acid groups. It is hypothesized, but the inventors do not intend to be bound by the hypothesis, that highly negatively charged proteins will repel one another, thus reducing the tendency of inclusion body recombinant proteins to aggregate in an aqueous medium, thereby producing the highly-desired water-soluble monomeric proteins. Following isolation in the presence of a weak denaturant, and desalting by either dialysis or gel filtration, this phase of the invention provides for fractionation of the thus derivatized recombinant proteins by molecular sieve or ion exchange chromatography.

Individual recovered proteins can be utilized in at least three fashions. In the first alternative, reversibly blocked sulfhydryl groups can be deblocked by suitable means, and the pure recombinant protein, still N-acylated, can be recovered by lyophilzation or can be stored frozen in solution. This phase contains several alternatives which include recovering the recombinant protein either still fully derivatized or partially derivatized or in nonderivatized form.

Figure 1:
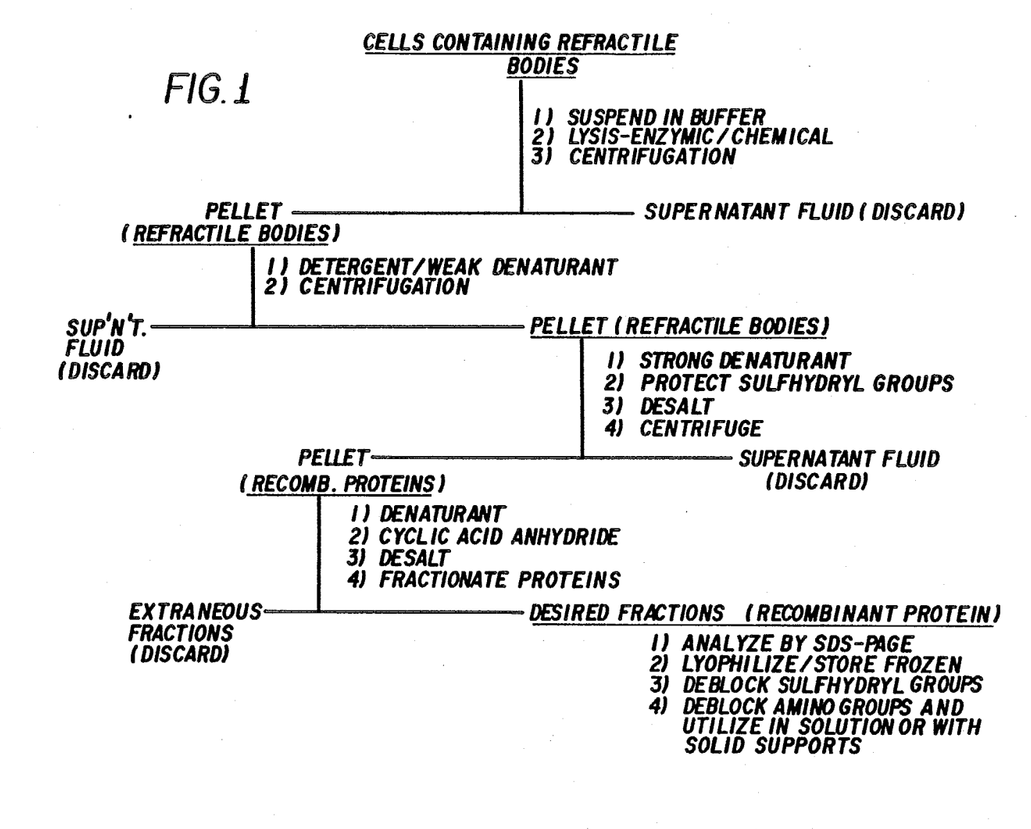
FIG. 1 is a flow sheet for a general procedure for isolating an active desired recombinant protein from host cells wherein this protein has been produced and deposited in the form of refractile bodies.
Figure 2:
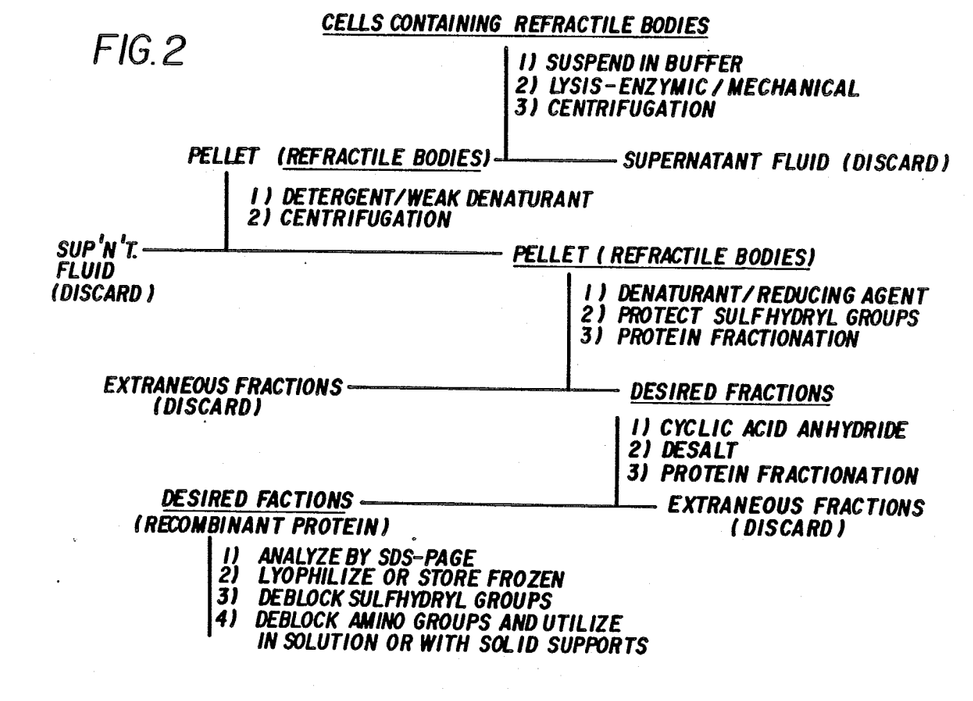
FIG. 2 is a flow sheet of a different procedure for isolating recombinant protein.

Another aspect of this invention is its flexibility in several of the phases of the protocol for recovery of pure recombinant proteins. As shown in FIG. 2, in the first phase, cell lysis can be accomplished in the absence of detergents and denaturants by a combination of enzymatic digestion and mechanical disruption. Further, in the third phase, preliminary purification of recombinant protein, following blocking of sulfhydryl groups, can be accomplished by protein fractionation on molecular sieves, rather than by aggregation following reduction of the concentration of a strong denaturant as shown in FIG. 1.

Another embodiment of the invention is its direction to the utilization of recovered pure recombinant proteins for diagnostic and other assays. The invention thus also comprises a process for coating solid supports such as microtiter plates, latex beads and the like with N-acylated recombinant proteins, deblocking the amino group in situ to restore antigenicity to the protein, and using the deblocked recombinant antigen for solid state assays, including enzyme-linked immunoassays (ELISA) and latex bead agglutination assays (LBA). These uses are outlined in FIG. 3 herein.

A. General Description of Source of Proteins to be Purified.

The invention herein described is directed to procedures which are useful in isolating, purifying, reactivating and using heterologous recombinant proteins that, subsequent to expression in microorganisms, appear in said cells as "refractile bodies" or "inclusion bodies," i.e., bodies that refract light and appear as bright spots when viewed through a phase contrast microscope. For the purposes of the present invention, these proteins are referred to as "refractile proteins" or "refractile body proteins" or "inclusion body proteins."

Where recombinant DNA technology is employed to induce host microorganisms to produce copious amounts of foreign proteins, such proteins are often referred to as "heterologous proteins" or "recombinant proteins" or "desired proteins." In the present invention, the term "protein" is meant to comprise all polypeptides and proteins. In the present invention, the words "refractile", "heterologous", and "recombinant" are used interchangably to denote a protein expressed in a host microorganism which is, at some stage of expression or purification, visible by phase contrast microscopy as a precipitate, regardless of the actual physical state of the protein at the point of reference, e.g., even after it has been converted from refractile to soluble forms by the process of the invention.

Various heterologous proteins expressed in microbial host cells, for example, HTLV-III/LAV virus antigen, HTLV-II virus antigen, HTLV-I virus antigen, and Feline Leukemia Virus antigen, appear as refractile bodies under commonly-found culture conditions. Other such examples include human and porcine growth hormones, the foot and mouth disease viral capsid protein, fibroblast interferon, human insulin, somatostatin, alpha, beta, and gamma interferons, and hepatitis B antigen (Builder et al., supra, and Old and Primrose, supra, pages 160–164). In short, included in the process of the invention are any heterologous proteins expressed by DNA technology in host microorganisms, wherein said proteins accumulate in the host cells as insoluble refractile bodies.

In the present invention, the term "host cells" include, but are not limited to, any microorganism which is used in recombinant DNA technology, including gram negative bacteria (selected from strains of *E. coli, Pseudomonas* spp. Proteus spp., Neisseriae spp., but preferably strains of *E. coli*), gram positive bacteria (selected from strains of *Bacillus subtilis,* Coryneformis spp., Actinomycetes spp., Streptomyces spp., Methylophilus spp., Cyanobacterium spp., preferably strains of *B. subtilis*), yeast such as *Saccharomyces cerevisiae,* fungi (selected from Neurospora, Aspergillus, and Podospera), and, algae such as Chlamydomonas (Old and Primrose, supra, chapters 3, 4, 8 and 10).

"Host cell" within the present context also refers to any form of the microorganisms in which expression of heterologous proteins have been induced by upward temperature shifts or other means, and is to be taken as including the entire cell culture in its growth medium, the harvested cell paste, a frozen sample of the paste, or a frozen and thawed sample of the paste, typically cells collected by centrifugation under standard conditions, e.g., up to 6,000×g for up to 60 minutes, most preferably 4,000×g for 30 minutes. B. Recovery of Refractile Body Recombinant Protein 1. Recovery of Refractile Bodies FIG. 1 is a flow sheet showing the general procedures involved in solving the problem of isolating an active desired protein from host cells, wherein this protein has been produced in response to an expression vector and thereafter deposited in the form of refractile bodies.

As shown in FIG. 1, because the refractile bodies are enclosed within host cells, it is desirable first to disrupt the cells to release the refractile bodies and make them available for recoveyy by, for example, centrifugation. In one aspect of the invention, partial purification of refractile bodies is obtained simply by ensuring that the host cell debris is sufficiently disrupted to remain in the supernatant phase during low speed centrifugation. In this aspect of the invention, cells are washed and resuspended in a buffer at pH 5 to 9.5, preferably about 8 to 9 using an ionic strength of the order of 0.01M to 2M, preferably 0.1–0.2M. Any suitable salt, preferably sodium cloride, can be used to maintain the proper ionic strength level. Ionic strength, the conventional measure of ion concentration, is desired as ½ of the sum of the product of the concentration of each ion present times the square of the charge thereon. Any suitable buffer may be used to maintain the pH in the correct range; Tris hydrochloride (Tris.HCl) buffer is a preferred buffer for maintaining the pH between 8 and 9 because of its buffering capacity in this range and because of its biochemical inertness.

The cells, while suspended in the foregoing buffer, are then lysed by techniques commonly employed for this purpose. Cell lysis is accomplished by a combination of enzymatic and/or chemical means. Enzymes commonly employed for this purpose include "Lysing Enzyme Mixture" from *Rhiz. solani*, "Lyticase" from *Arth. luteus*, "Mutanolysin" from *Strep. globisporus*, "Lysostaphin" from *Staph. staphlolyticus*, deoxyribonuclease (DNAse) from bovine pancreas and/or spleen, and Lysozyme (muramidase). It is preferred to employ Lysozyme plus DNAse. It is also desirable to protect the desired proteins from attack by the host cell's own proteases. This can be accomplished by contacting the lytic mixture with a protease inhibitor, such as the lung protein apoprotinin, soybean trypsin inhibitor, or phenylmethylsulfonylfluoride (PMSF), preferably apoprotinin and PMSF.

It is also desirable to disrupt hydrophobic structures in the cell wall/membrane with a detergent, i.e., a surface active agent. Cell lysis is aided by a nonionic detergent such as the polyoxyethylene ether types, including Triton X-15 through Triton X-405, Triton N-101, Triton WR-1339, Lubrol-PX, preferably Triton X-100 in a concentration sufficiently low so as not to disrupt the refractile bodies at the cell lysis stage. Detergent concentrations are of the order of 0.005–1%, preferably 0.1–0.2%.

When it is judged that the cells are sufficiently disrupted so that there will be remaining no, or a minimum of, cellular fragments of size sufficiently large so as to sediment, the lysis suspension is centrifuged at low speed, around 500 to 6500×g, preferably 5000–6000×g, in a standard centrifuge for a suitable time depending upon volume, usually for 20–30 minutes. The resulting pellet contains refractile bodies, usually (as determined by phase contract microscopy) still contaminated with adsorbed host cell proteins and membrane fragments.

Contaminating material can be removed by repeated suspension of the refractile body pellets in suitable buffer, preferably twice with 0.1–0.2% Triton X-100 in Tris.HCl buffer, pH 8–9; once with 0.15–2M NaCl in Tris.HCl buffer, pH 8–9; once with Tris. HCl buffer (pH 8–9) containing a chelator such as 1–10 mM ethylenediaminetetracetate (EDTA) and an ionic detergent selected from among commercially available (Pierce Chemical Co.) SDS, LDS, CHAPS, CHAPSO, and Zwittergents, preferably Zwittergent 3-14 (0.05–0.3%, preferably 0.1–0.2%); and once with a weak denaturant solution such as 2–10M, preferably 5–6M, urea in Tris. HCl buffer pH 8–9.

"Denaturing solution" refers to a solution that contains a "denaturant," "denaturant" referring herein to those chaotropic components that, in aqueous solution, are capable of changing the conformation of proteins either through altering the state of hydration, the solvent environment, or the solvent-surface interaction. Examples of denaturants include urea, guanidine.HCl, and sodium thiocyanate, but include as well detergents, i.e., surface-active agents, as listed above. Some of the listed reagents are strong denaturants, while others are weaker. The concentration of any of these will, of course, directly affect its strength and effectiveness.

Although there can be no precise dividing line between "strong" and "weak," generally, strong denaturants more completely unfold proteins from their native conformations. The most commonly used strongly denaturing environment useful in dissolving refractile proteins is fairly high (4–9M) concentrations of the ionic denaturant, guanidine.HCl. Urea is the most frequently used example of a relatively weak denaturant, as even fairly high, e.g., 7M, concentrations permit the retention of some protein secondary structures. Accordingly, as set out in FIG. 1, washing refractile bodies with a solution of weak denaturant, e.g. urea, will remove contaminating host cell proteins, while not dissolving the refractile bodies themselves.

2. Derivatization of Sulfhydryl Groups

It is desired to protect the free sulfhydryl groups of refractile body proteins against undesirable side reactions such as air oxidation to sulfonic acids and disulfide cross-linking of proteins, as well as against reaction with cyclic acid anhydrides in phase 3 below.

Accordingly, the refractile bodies prepared as above are dissolved in a strong denaturing solution, preferably guanidine.HCl (6–7M in Tris. HCl bufer, pH 8–9), in the presence of a reducing agent designed to maintain sulfhydryl groups in their reduced state. Typical reducing agents include, but are not limited to, 2-mercaptoethanol, dithiothreitol (DTT), cysteine, or sodium phosporothiolate. See also Means & Feeney, *Chemical Modification of Proteins*, Holden-Day, Inc., San Francisco, 1971, Chapter 8. 2-Mercaptoethanol (0.1–1.0M) is preferred. Thereafter, free sulfhydryl groups are derivatized either reversibly or irreversibly, the choice being based upon whether or not an individual recovered recombinant protein requires, for biological or immunologic activity, that its sulfhydryl groups be in the free state. If such freedom is not necessary, irreversible derivatization is selected because of the ease and completeness of the chemical addition of the protecting groups, and because of the chemical stability of the irreversible derivatives.

Irreversible alkylation of recombinant protein sulfhydryl groups is accomplished, according to standard procedures, typically by contacting said protein with an excess (preferably 5-10-fold molar excess) of an alkylating agent, selected from among iodoacetic acid, iodoacetamide, N-ethylmaleimide, 3-bromopropionic acid, acrylonitrile, preferably iodoacetic acid, at room temperature for 0.5-2 hours, preferably 1 hour, with an alkaline pH (pH 8-9) being maintained by addition of a strong alkali, preferably NaOH, during the reaction. See Means & Feeney, supra, Chapter 6 and 8.

If it is desired later to remove protecting moieties from the sulfhydryl groups of recombinant protein, then reversible derivatization of the recombinant protein sulfhydryl groups can be accomplished by contacting said sulfhydryl groups with a molar excess of one or another agent selected from among glutathione, cysteine, 5,5'-dithiobis(2-nitrobenzoate), or o-iodosobenzoate, with which the sulfhydryl group will form a disulfide linkage. Alternatively, free sulfhydryl groups can be converted to the S-sulfonate derivative by reaction with sodium sulfite, or to the S-sulfenylsulfonate derivative by reaction with sodium tetrathionate. Glazer et al., *Chemical Modification of Proteins*, in Work et al., (eds.) *Laboratory Techniques in Biochemistry and Molecular Biology*, Elsevier, Amsterdam, (1976) pp. 108-110. At appropriate times, the disulfide, S-sulfenylsulfonate and S-sulfonate derivatives can be restored to the free sulfhydryl state by contacting said derivatives with reducing agents that have high reducing potentials, preferably 2-mercaptoethanol and DTT. Reversible blocking of sulfhydryl groups will allow a controlled refolding of the recombinant proteins and formation of intramolecular disulfide bonds, thereby increasing the chances of achieving the correct native conformation.

According to the embodiment set out in FIG. 1, it is possible to achieve partial purification of the recombinant protein following derivatization of sulfhydryl groups by selective precipitation by reducing the concentration of the strong denaturant in an alkaline medium. This is most preferably done by dialyzing the derivatization reaction mixture against sodium borate buffer. The buffer concentration is 0.01-1M, preferably 0.05-0.10M, and the pH is 8-10, preferably 8.5-9.5. The precipitated protein is recovered as a pellet by low speed centrifugation as described hereinabove.

3. Derivatization of Amino Groups with a Cyclic Dicarboxylic Acid Anhydride While solubility of refractile body recombinant protein, once achieved, is often maintained when the solubilized protein is exchanged into a more weakly denaturing solution, such as high concentrations of buffered urea, initial solubility in this same weakly denaturing medium is impractical. Whether for thermodynamic or kinetic reasons, refractile body proteins do not dissolve within a reasonable time under these less drastic denaturing conditions. Thus, strongly denaturing solutions, such as guanidine.HCl are required for initial solubilization, and weakly denaturing solutions can thereafter maintain solubility (Olson, supra). In order to overcome the solubility problem of refractile body protein, and to do so without necessarily using denaturants, a large negative charge is imposed on the recombinant protein, the negative charge promoting the disaggregation of the protein into a water-soluble, monomeric state.

This aspect of the invention is directed to contacting free amino groups of the desired protein with particular cyclic dicarboxylic acid anhydrides under alkaline conditions, this contact leading to the reversible formation of N-acyl groups that terminate in carboxylic acid groups, all of which being ionized and thus negatively charged at all pH values numerically greater than the ionization constant of weak organic acids, i.e., above a pH of about 4.

The reversibility of aceylation of amino groups by cyclic acid anhydrides depends on the presence of the protonated carboxyl group specifically oriented to particulate as an intramolecular catalyst of the hydrolytic reaction. This orientation may be the result of cis-configuration of the carboxyl group about the carbon-carbon double bond, or an arrangement of adjacent carboxyl groups on a hydrophthalic ring. Glazer et al. supra., pp. 79-84.

The general structures for cyclic acid anhydrides with the aforementioned desirable properties can be represented as follows:

where $R_1$ and $R_2$ in the left figure can be selected from among any combination of hydrogen atom and alkyl group. In the structure shown on the right, the 4,5-bond may be either a single or double bond.

As a consequence of these conditions, examples of appropriate cyclic acid aid anhydrides include, but are not limited to, citraconic anhydride (monomethyl maleic acid) maleic anhydride, dimethylmaleic anhydride, exo-cis-3,6-endoxo-$\Delta^4$-hexahydrophthalic anhydride, and exo-cis-3,6-endoxo-$\Delta^4$-tetrahydrophthalic anhydride. The particular anhydride that is most suitable for a particular recombinant protein can be selected for tests that are within the skill of the art.

The recombinant protein is dissolved in high concentrations (6-9M, preferably 7-8M) of weakly-denaturing solution, preferably urea in sodium borate buffer (1-100 mM, preferably 40-60 mM) at pH 8-10, preferably pH 8.5-9.5. After completion of solubilization, the recombinant protein is contacted with an excess (5-100-fold molar excess, preferably 40-60-fold molar excess) of cyclic dicarboxylic acid anhydride, added in aliquots representing 1/40th of the total anhydride to be added, while maintaining the pH at 8-10, preferably at pH 8.5-9.0, by the periodic addition of strong alkali, preferably 5N NaOH.

4. Protein Fractionation Following Derivatization

Following completion of the N-acylation reaction described above, the reaction mixture is desalted to remove excess cyclic dicarboxylic acid anhydride and any of its hydrolytic products, i.e., the dicarboxylic acid itself. This can be accomplished, according to the invention, by dialysis of the reaction mixture against an alkaline buffer such as sodium borate (0.01-0.20M, preferably 0.05-0.10M; pH 8-10, preferably pH 8.5-9.0).

Alternatively to, or subsequent to, the dialysis, the recombinant protein double- derivative can be recovered by fractionation on chromatography matrices of either the molecular sieve or ion exchange types. Suitable molecular sieve columns include, but are not limited to, Ultragels (LKB Products), Fractogels (Pierce Chemical Company), and Sepharose, Sephadex and Sephacryl (Pharmacia Fine Chemicals). In a preferred embodiment, the recombinant protein derivative is fractionated on an Ultragel ACA 3 gel column equilibrated with sodium borate buffer (0.01–1.00M, pH 8.5–9.5), and the elution profile is monitored at a wave length of 280 nm, the region of maximum ultraviolet absorption of proteins. The molecular weight of the eluted recombinant protein is estimated by reference to the elution volumes of commonly used standard proteins.

Suitable ion exchange columns include, but are not limited to, Fractogels TSK-DEAE (Pierce Chemical Company) or DEAE-Sepharose and DEAE-Sephacel (Pharmacia Fine Chemicals). In a preferred embodiment, recombinant protein is fractionated on a column of Fractogel TSK-DEAE-650 equilibrated in sodium borate buffer (0.01–0.10M, pH 8.5–9.5), proteins being eluted by a salt gradient from 0.3 to 1M sodium chloride in the above-described sodium borate buffer. The Fractogel TSK-DEAE ion exchanger is preferred because of its greater rigidity and consequently faster flow rates.

The recombinant protein solutions eluting off the chromatography columns can either be lyophilized to recover the protein in powdered form or stored frozen, typically at −20° to −180° C.

5. Deblocking of Amino and Sulfhydryl Groups

In another aspect of the invention, the abovedescribed pure recombinant protein can be restored to its native state by deblocking, i.e. by removing the blocking groups from the sulfhydryl groups (where derivatization was reversible), and by removing the acyl carboxylic acid groups from the amino groups. For example, N-acyl carboxylic acid groups of recombinant proteins can be hydrolyzed by contacting said protein with acidic buffers at pH values between 3 and 6, preferably 4.0–5.5, for an appropriate length of time at a suitable temperature. Where the ratio of ug of protein to umoles of acidic buffer is about 1:15, hydrolysis is complete in about 24 hours at about room tempeature (25° C.), and in about 16 hours at about 37° C.; hydrolysis is about 50% complete in about 1 hour at 37° C. and about 2 hours at about 25° C. Deblocking of the amino groups is required in order that the recombinant protein by fully antigenic. Citraconylated HTLV-III/LAV antigen, for example, has only about half the antigenicity of the deblocked protein, as judged by ELISA assays to be described below.

It is an aspect of the invention that some refractile body recombinant protein will aggregate following removal of the repelling acyl carboxylic acid groups, particularly when the protein is in a concentrated solution. It is an important aspect of the invention, therefore, that such isolated proteins not be deblocked until, as described below, they are ready to be adsorbed onto a solid support. In other instances, a recombinant protein used for vaccine or therapeutic purposes should be deblocked under conditions that allow proper refolding into a biologically active conformation and that preserves its solubility properties.

With some recombinant proteins, e.g., HTLV antigens, it may not be necessary to deblock the sulfhydryl groups in order to achieve full biological activity. But where, according to the nature of the recombinant protein antigen, it may be necessary to deblock sulfhydryl groups, the invention is also directed to the restoration of sulfhydryl groups to their native state. According to the invention, this can be accomplished without regard to the presence or absence of N-acyl carboxylic acid moieties on the recombinant protein. According to standard methdos (Means & Feeney, supra, Chapter 8), S-sulfonated and S-sulfenylsulfonated recombinant proteins can be reduced to their free sulfhydryl counterparts by contacting about 1 mole of protein in 0.02–1M Tris.HCl or sodium phosphate buffers, pH 7.0–7.6, with a reducing agent such as 2-mercaptoethanol, dithiothreitol, sodium phosphorothiolate, sodium borohydride, sodium sulfite, preferably 0.1–0.7M 2-mercaptoethanol for 15 minutes at 37° C. or 60 minutes at 25° C. Thereafter, the reaction mixture is desalted by dialysis against a suitable buffer. Similar standard procedures will reduce disulfide linkages to moieties such as cysteine, glutathione, and 5, 5'-dithiobis(2-nitrobenzoate).

6. An Alternate Scheme for Recovering Recombinant Protein

Another aspect of the invention is its flexibility with regard to several steps of the protocol for the recovery of pure refractile body recombinant proteins in derivatized form. In the alternative approach shown in FIG. 2, host cell lysis is carried out by a combination of enzymatic and mechanical means, instead of the enzymatic-chemical combination used in Figure 1.

In FIG. 2, following washing of cells with Trisbuffered saline as in FIG. 1, cells are suspended in PMSF (0.5–2.0M), DTT (0.01–1.0M), Triton X-100 (0.05–0.3%), EDTA (1–20 mM, in Tris.HCl buffer (0.01–0.10M, pH 8–9), then lysed by contact with lytic enzymes as in FIG. 1 together with mechanical disruption by sonic oscillation, homogenization, grinding in mills, or exposure to a pressure cell; no denaturant is used.

In another aspect of the process of FIG. 2, following derivatization of the sulfhydryl group of the recombinant proteins, partial purification of the desired protein is achieved, not by the precipitation protocol of the process of FIG. 1, but by fractionation on a molecular sieve in the presence of a weak denaturant, preferably Sepharose 6B-CL (Pharmacia Fine Chemicals) operated in the presence of 8M urea. This matrix is particularly suitable for recovery of proteins that are insoluble or aggregated in ordinary aqueous buffer systems.

C. Use of Purified Recombinant Proteins in Diagnostic Devices

It is extremely useful to be able to produce a diagnostic device comprising a solid support to which is bound a pure recombinant protein antigen. This device is appropriate for carrying out solid state immunoassays and agglutination assays for antibodies to such antigens that are present in the sera and other body fluids of humans and animals. The production of such diagnostic devices according to the present invention is summarized in the FIG. 3 flow sheet.

Figure 3:
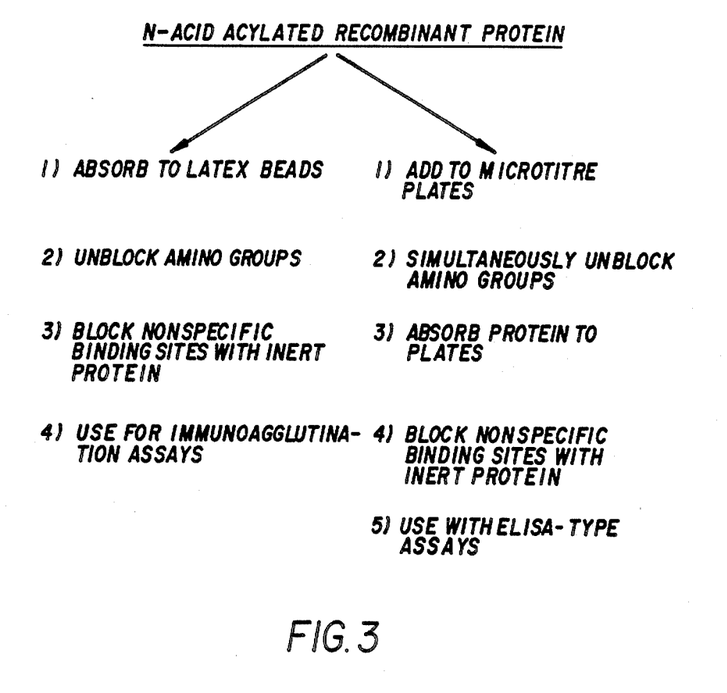
FIG. 3 is a flow sheet demonstrating procedures for the preparation of device suitable for solid state and agglutination assays involving the recombinant protein recovered by the processes of FIGS. 1 and 2.

In one aspect of the invention as described in FIG. 3, purified recombinant protein is adsorbed to the wells of microtiter plates. Typically, such plates include, but are not limited to, polystyrene or polypropylene. An aliquot of a solution of N-acylated recombinant protein, preferably N-citraconylated recombinant protein, dissolved in alkaline buffer, preferably sodium borate (0.01–0.10M, pH 8.5–9.5), is added to each well of a microtiter plate. The amount of recombinant protein delivered to each well is adjusted according to the biological activity of this protein and according to the sensitivity of the subsequently-employed assay. Typically, for an ELISA assay for HTLV antibodies, 0.1 to 1.0 ug of protein in 0.01–0.10 ml. of solution per well is sufficient.

Following addition of the antigen, according to the invention a 10–20-fold molar excess of a weak acid buffer is added to each well in order to hydrolyze the acid acyl groups from the amino groups of the recombinant protein. The pH of the hydrolyzing buffer can range from 3.5 to 6.0, preferably pH 4 for sodium acetate buffer and pH 5.5–5.6 for sodium citrate buffer. The plates are incubated for period of time required to completely hydrolyze N-acid acyl groups, as determined by a standard trinitrobenzenesulfonic acid (TNBS, Means & Feeney, supra, p. 217) test for free amino groups. This will occur in about 16 hours at 37° C. or 24 hours at 25° C.; the shorter time is preferred. After adsorption of the deacylated recombinant protein to the well is complete, the solution in the well is aspirated to waste.

According to standard procedures, nonspecific binding sites on both the recombinant protein and the plastic surfaces of the well are blocked with a dilute solution of, for example, pure bovine serum albumin (typically, an equal volume of a 0.1–2% solution in standard phosphate-buffered saline, pH 7.6). The albumin solution is then aspirated to waste, and the wells permitted to air dry.

In another aspect of the invention, there is produced a diagnostic device comprising latex beads to which is adsorbed recombinant protein. This device is particularly suitable for latex bead agglutination assays. According to the invention, N-acylated recombinant protein antigen, preferably citraconylated recombinant protein, at a concentration of 30 ug/ml is physically adsorbed to latex beads (preferably polystyrene beads, 0.1–1.0 microns in diameter) as a 1–4% suspension in alkaline buffer, typically sodium carbonate buffer, pH 8.5–9.5. Following adsorption of the protein to the beads, i.e., during 16 hours at 25° C. with stirring, a weak acid buffer such as sodium acetate buffer (0.05–1.0M, pH 3.5–4.5), is added to hydrolyze the N-acid acyl groups of the recombinant proteins. The antigen-coated latex beads are isolated by low speed centrifugation, the supernatant fluid is aspirated to waste, and the beads are then resuspended in a solution of a protein designed to adsorb to nonspecific binding sites on the surface of the latex beads. According to the invention, this is accomplished by suspending the beads in a 0.5–2.0% (w/v) solution of bovine serum albumin in a standard phosphate buffered saline (PBS, pH 7.6) that also contains 0.01–0.10% nonionic polyethoxyether detergent, preferably Tween 20. The final concentration of the suspension of beads is 0.1–1.0% by weight, preferably 0.5–0.6%. The beads should be stored in a refrigerator at 4° C.

D. Assays Employing Diagnostic Devices

Diagnostic devices produced by the present invention can be utilized in a variety of assays.

In one aspect of the invention, microtiter plates, whose wells are coated with recombinant protein antigens obtained according to the invention, are particularly useful for ELISA assays for antibodies to said antigens in the body fluids and tissues of man and animals. ELISA tests are carried out according to E. Engvall, *Methods in Enzymology* 170: 419–438 (1980), which is herein incorporated by reference.

In this aspect of the invention, aliquots of fluids to be analyzed, in suitable dilutions, are added to wells containing adsorbed recombinant protein antigens. After the antigen-antibody reaction is complete, typically after incubation at 25°–40° C. for 30–120 minutes, the fluid in the well is aspirated to waste, and the well washed once with PBS pH 7.6.

Thereafter, there is added to each well a solution of a second antibody, e.g. anti- human IgG, to which is conjugated covalently a reporter molecule, selected according to the requirements of the assay, preferably an enzyme such as horseradish peroxidase or alkaline phosphatase.

After the reaction between the primary antibody and secondary antibody is complete (incubation for 0.5–24 hours at 25°–40° C.), the wells are washed with PBS, and the reporter molecule detected, typically using the appropriate chromagen solution, preferably p-nitrophenylphosphate for the alkaline phosphatase reporter, and hydrogen peroxide plus diaminobenzidine and copper nitrate for the peroxidase reporter. Absorbancy is then read in a microtiter plate spectrophotometer. Any of the reporter molecules known to the art may be used to practice this aspect of the invention.

In another aspect of the invention, latex beads, coated with recombinant protein antigen obtained according to the processes hereinabove described, are used to assay for antibodies to said proteins that are present in the body fluids of humans and animals. The latex bead agglutination test is carried out according to Williams and Chare, *Methods in Immunology and Immunochemistry*, (1977) pp 115–125, incorporated by reference herein. According to the invention, a small aliquot (5–50 ul) of serum or other body fluid is mixed with a small aliquot (3–ul) of a suspension of antigen-coated latex beads on a glass slide. According to the invention, it is preferred slowly to rotate the slide at 25° C. for the period required for complete reaction of antigen with antibody, typically 5–10 minutes. A positive end point, according to the invention, is macroaggregation of the latex beads that is visible to the unaided eye, or microscopically.

Having now generally described the invention, the same will be more clearly understood by reference to the following examples, none of which are intended to be limiting unless so specified.

Examples 1 and 2 relate to that aspect of the invention which comprises solubilization of refractile body recombinant proteins and recovery of such proteins in a purified derivatized form.

Examples 3 and 4 relate to that aspect of the invention that comprises coating of the purified recombinant protein antigens to solid supports, and utilization of such coated solid supports in several varieties of assays.

All of the examples relate to specific heterologous recombinant proteins that have been purified by the process of the invention. The details of the purification will vary, of course, with specific proteins used. Although the procedure of the invention will be similar in all cases, certain details, such as, for example, the selection of the denaturing agent and solubilization of the desired protein, the selection of the appropriate sizing gels or ion exchange resins, as well as the ionic strength and pH conditions appropriate in each step will be dependent on the nature of the protein. However, recombinant proteins share enough properties in common that these minor alterations will suffice to adapt the procedure to a particular protein in question.

All literature references cited in these examples are incorporated into this application by reference.

EXAMPLE 1

Procedure for Isolation of Derivatized Refractile Body Recombinant Protein Antigens in Water-Soluble Forms—The Process of FIG. 1

E. coli cells were collected by centrifugation at 4,000×g for 30 minutes, washed once with 0.15M NaCl-50 mM Tris.HCl buffer, pH 8.5, and resuspended in 4 volumes of 50 mM Tris. HCl buffer, pH 8.5.

Cells were then lysed with Lysozyme, two mg/g pelleted bacteria, in the presence of apoprotinin, 30 mg/g pelleted bacteria. Cells were further disrupted by the addition of 0.2% Triton X-100 and DNAse, 70 mg/g pelleted bacteria. Following stirring for 60 minutes to allow maximum lysis, the recombinant proteins in the forms of insoluble aggregates, i.e. refractile bodies, were collectd by centrifugation at 6,000×g for 30 minutes. These aggregates were washed twice with 0.2% Triton X-100 in 50 mM Tris.HCl buffer, pH 8.9, once with 1M NaCl in 50 mM Tris.HCl buffer, pH 8.9, once with 0.2% Zwittergent 3-14 and 5 mM EDTA in 50 mM Tris.HCl buffer, pH 8.9, and once with 6M urea in 50 mM Tris.HCl, buffer pH 8.9.

The inclusion bodies were dissolved in 6M guanidine.HCl and 0.5% 2-mercaptoethanol in 50 mM Tris.HCl buffer, pH 9.0. Free sulfhydryl groups were alkylated with a 5-fold molar excess of iodoacetic acid over 2-mercaptoethanol at 25° C. for one hour. A pH of 8.5 was maintained by the addition of 5N NaOH during the reaction. A partial purification of the alkylated protein was achieved by selective precipitation of such protein during dialysis against 50 mM sodium borate buffer, pH 9, to remove the guanidine.HCl. The protein was recovered as a pellet by low speed centrifugation.

To 100–150 mg of recombinant protein dissolved in 100 ml of 8M urea in 50 mM sodium borate buffer, pH 9.0, was added with constant stirring at 25° C., 4 ml of citraconic anhydride in 100 ul aliquots, the pH being maintained at 9.0 by the addition of NaOH. Following an additional 30 minutes of reaction time to ensure completion of the reaction, the reaction mixture was desalted either by dialysis against 50 mM sodium borate buffer, pH 8.5–9.0, or by gel filtration on Trisacryl GF 05 (LKB Products).

Figure 4:
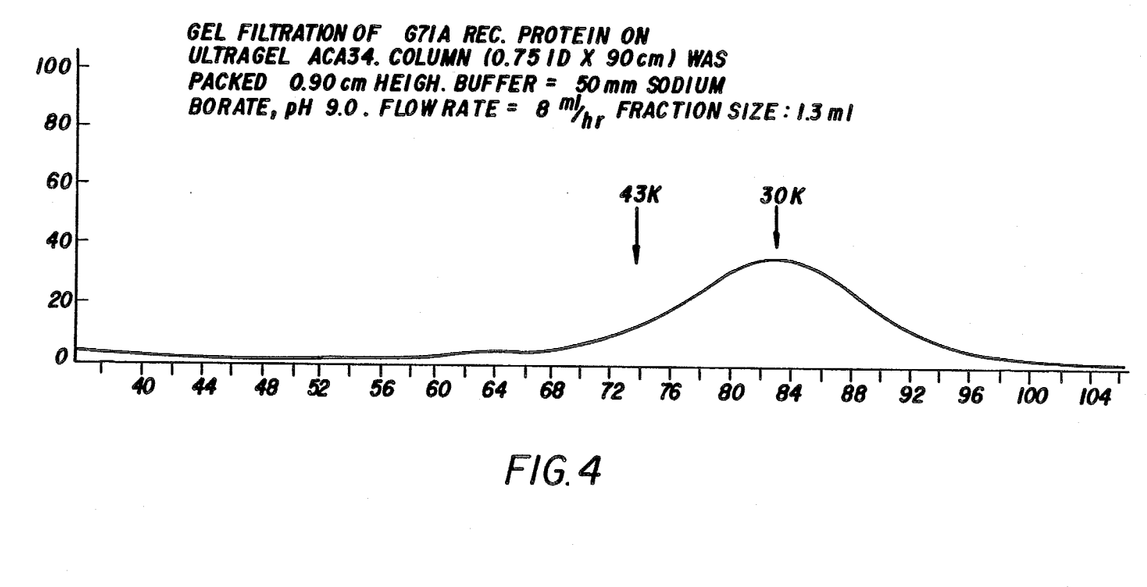
FIG. 4 shows the elution profile of S-alkylated, N-citraconylated HTLV-III/LAV recombinant protein from an Ultragel ACA 34 column.
Figure 5:
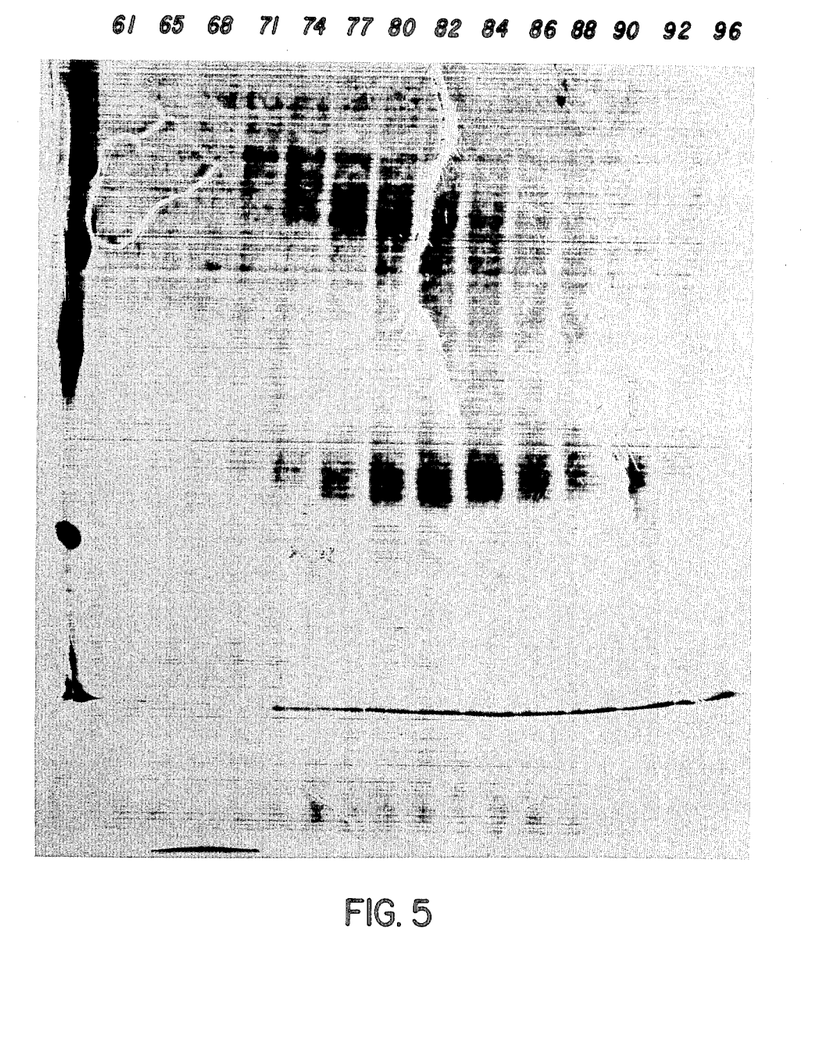
FIG. 5 shows an analysis by SDS-PAGE of the recombinant protein recovered in FIG. 4.

Citraconylated protein, 5 mg in 1 ml of a solution, was purified by filtration through a molecular sieve column of Ultragel ACA 34 (0.75 cm I.D.×90 cm) equilibrated with 50 mM sodium borate buffer, pH 9.0. The elution profile was monitored by following the absorbancy at 280 nm, and compared with the elution profile of standard proteins. As shown in FIG. 4, recombinant HTLV-III/LAV antigen eluted at a position corresponding to a monomeric Mr of about 35,000. Analysis of the peak gel filtration fractions by SDS-PAGE, which separates proteins on the basis of mass, showed the presence of one major band of Mr of about 35,000, plus several contaminating higher molecular weight species (FIG. 5).

Figure 6:
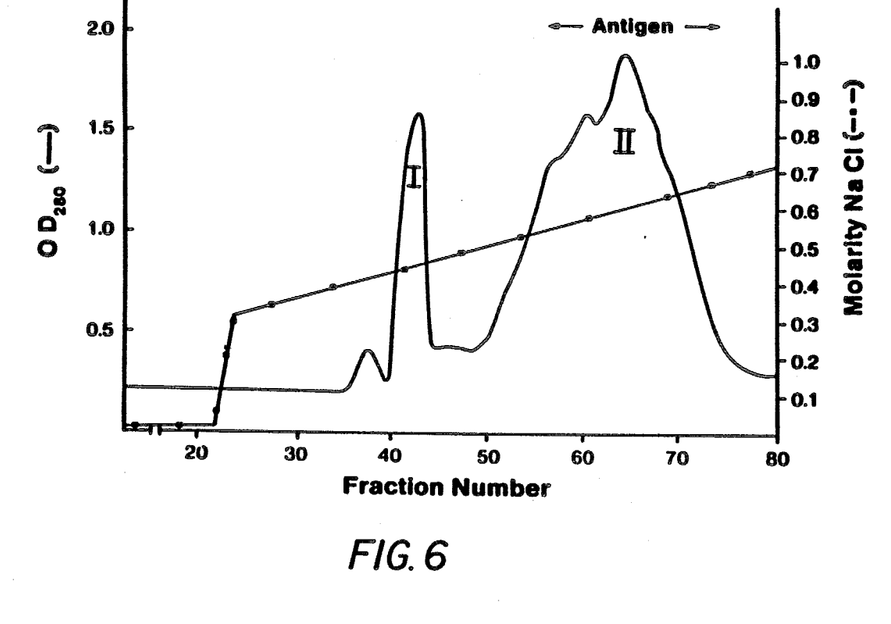
FIG. 6 shows the elution profile of S-alkylated, N-citraconylated HTLV-III/LAV recombinant protein from an anion exchanging Fractogel DEAE-TSK column.

Citraconylated proteins were also fractionated on ion exchange columns. In one example, 100 mg of citraconylated protein in 100 ml of 50 mM sodium borate buffer, pH 9.0, was applied to a 2.5×17 cm column of Fractogel DEAE-TSK 650 at a flow rate of 2 ml/minute, and eluted by 500 ml of a 0.3 to 1M NaCl gradient in 50 mM sodium borate buffer, pH 9.0. The HTLV-III/LAV antigen (30 mg) was eluted between 0.4 and 0.5N NaCl (peak II in FIG. 6). Minor contaminating proteins (peak I) were also present. The recombinant protein(s) in peak II from FIG. 6 was analyzed by SDS-PAGE (FIG. 7), the major band corresponded to a protein of Mr about 35,000 upon decitraconylation.

Figure 7:
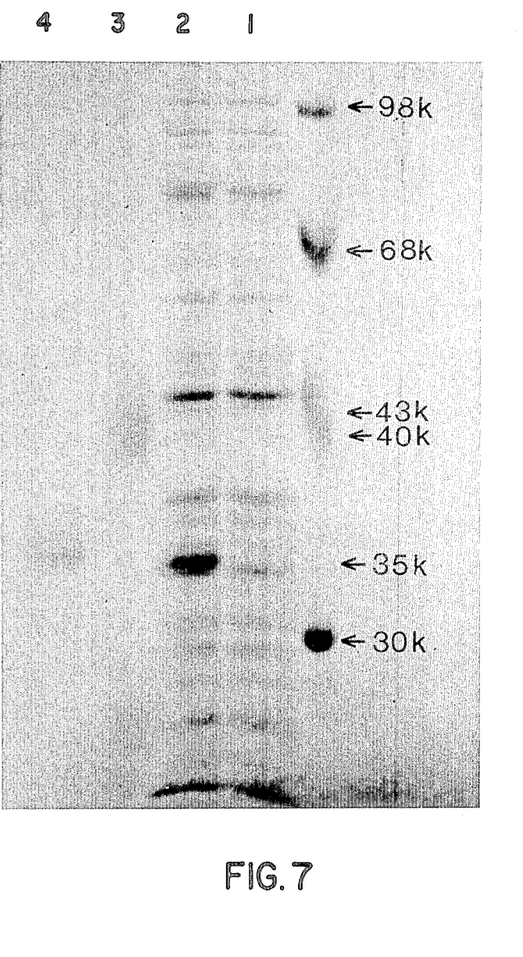
FIG. 7 shows an analysis by SDS-PAGE of the recombinant protein recovered in FIG. 6.

FIG. 7 is a photograph of Coomassie blue-stained 10% polyacrylamide gel of transfected E. coli and purified HTLV-III/LAV (Delta G71A) polypeptides. Lane 1 is the result of an SDS-PAGE analysis of 80 ug of E. coli transfected with Lambda PL and the gene coding for HTLV-III/LAV polypeptide. Lane 2 is the result of an SDS-PAGE analysis of 80 ug of E. coli transfected with Lambda PL and the gene coding for HTLV-III/LAV polypeptide, following induction. Note the increase in expression of the 35,000 Mr protein. Lane 3 shows the result of an SDS-PAGE analysis following citraconylation, but without deblocking. In Lane 4, the protein of Lane 4 has been decitraconylated under acid conditions.

EXAMPLE 2

Procedure for Isolation of Derivatized Refractile Body Proteins in Water-Soluble Forms—The Process of FIG. 2

A culture of E. coli grown in LB broth at 32° to an A550 of 0.5, was induced to express HTLV-III antigen by a temperature shift to 42° for 1.5 hours. Cells were collected by centrifugation at 4,000×g for 30 minutes, washed once with Tris-buffered saline, then resuspended in 50 mM Tris.HCl buffer, pH 8.5, containing 1 mM PMSF, 50 mM DTT, 10 mM EDTA, and 0.2% Triton X-100. The cells were then lysed by digestion with Lipozyme and by brief repeated sonications. The expressed protein(s), as insoluble aggregates, were collected by centrifugation at 5,000×g for 30 minutes. After several successive washings with Tris.HCl-buffered 0.2% Triton X-100 and 6M urea, the protein aggregates were solubilized in 8M urea and 1% 2-mercaptoethanol in 50 mM Tris.HCl buffer, pH 8.5.

Free sulfhydryl groups of recombinant proteins were alkylated by the addition of a 10-fold molar excess of iodoacetic acid at 25° C. Partial purification of the alkylated protein antigen was achieved by gel filtration through a Sepharose 6B-CL column in the presence of Tris.HCl-buffered 8M urea.

The column factions containing the alkylated recombinant protein(s) were then treated at 25° C. for 1.5 hours with a 50-fold molar excess of citraconic anhydride in a solution of 8M urea in sodium borate buffer, pH 8.5. Following extensive dialysis of this reaction mixture against 0.1M sodium borate buffer pH 8.5, antigen was further purified by gel filtration on a Fractogel column equilibrated in the same buffer. Citraconylated HTLV-III/LAV proteins eluted in a position corersponding to a Mr of about 35,000, when compared to a 30,000 dalton molecular weight standard.

EXAMPLE 3

Figure 8:
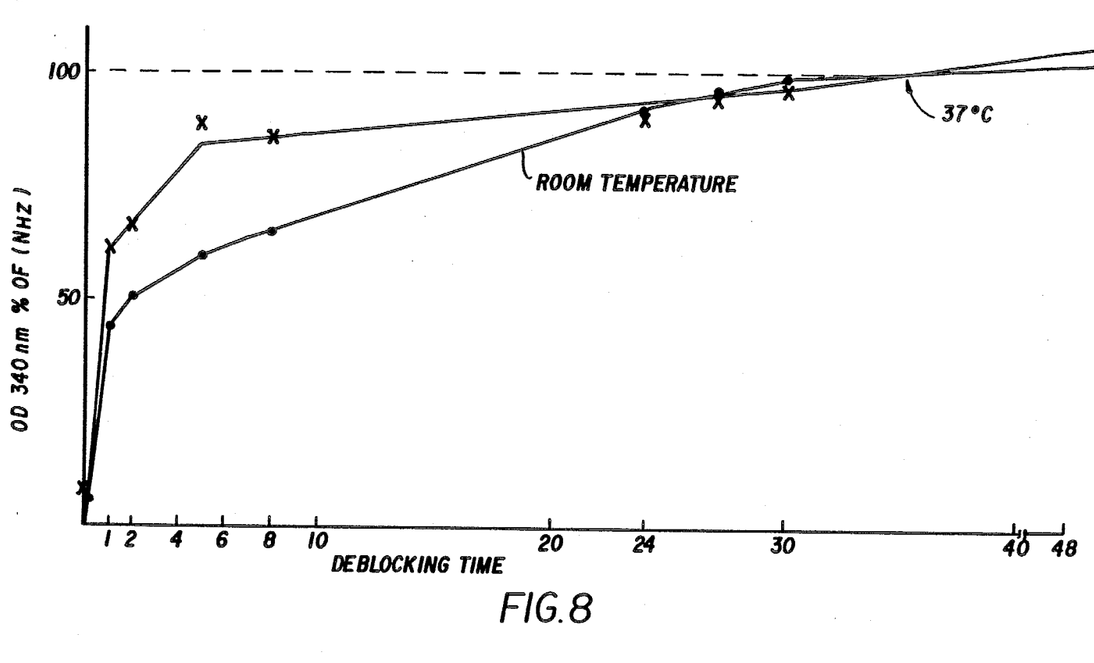
FIG. 8 shows the kinetics of the decitraconylation of recombinant HTLV-III/LAV protein at 37° C. and 25° C. in sodium citrate buffer, pH 5.5.

Coating of Microtiter Plates with Citraconylated Recombinant Protein and Use in an ELISA S-alkylated or free sulfhydryl citraconylated recombinant protein antigen (50 ul of a 10 ug protein/ml solution in 25–50 mM sodium borate buffer, pH 9.0) were added to each well of a polystyrene microtiter plate, followed by an equal volume of 0.15M sodium citrate buffer, pH 5.5–5.6. The plates were incubated for a period sufficiently long completely to hydrolyze citraconyl groups from amino groups (16 hours at 37° C.

or 24 hours at 25° C., as determined by a standard TNBS test for free amino groups (cf., FIG. 8). After aspirating the reaction mixture to waste, the non-specific binding sites on the adsorbed recombinant protein and on the polystyrene surfaces themselves were blocked by incubating each well with a solution of 1% (w/v) pure bovine serum albumin in PBS, pH 7.6, containing 0.06% Tween 20 detergent. The solution was aspirated to waste, and the wells air dried.

Aliquots of blood sera, appropriately diluted with PBS buffer, pH 7.6, were added to wells, and incubated at 37° C. for 1 hour. The excess fluid was aspirated to waste, and the cells washed once with PBS buffer, pH 7.6. Thereafter, peroxidase-conjugated anti-human IgG was added (E. Engvall, supra). The plates were incubated, washed, and the peroxidase chromagen added. The absorbancies at 550 nm were determined in a microtiter plate spectrophotometer (Dynatech MR600). The results (Table I) showed that all HTLV-III/LAV positive samples (confirmed by immunoblot and radioimmunoprecipitation assays according to L.W. Kitchen et al., Nature 312:166 (1984)) had ELISA absorbancies greater then 0.41, with all but 6 samples greater than 1.00. All HTLV-III/ LAV-negative samples i.e., background absorbancies, had readings below 0.24. Therefore, setting a cut-off ELISA reading at 0.30, the ELISA test with decitraconylated recombinant HTLVIII/LAV antigen was 100% accurate.

Figure 9:
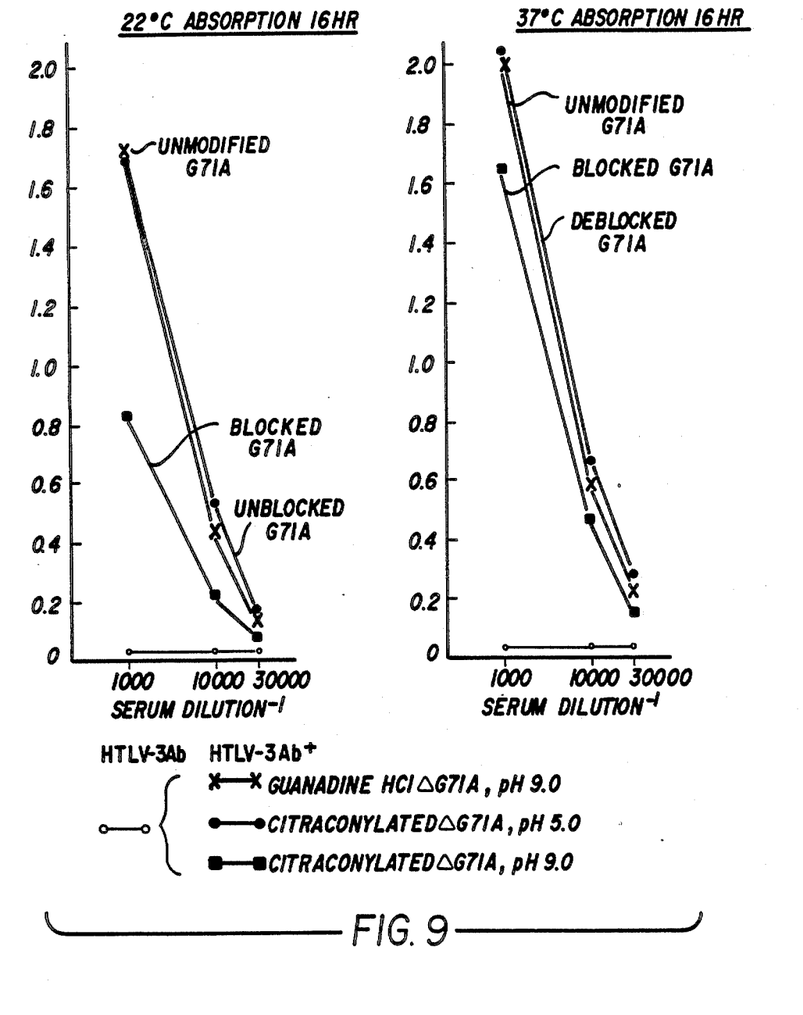
FIG. 9 compares the immunoreactivity of citraconylated HTLV-III/LAV protein antigen with the decitraconylated form of the protein. cl DESCRIPTION OF THE PREFERRED EMBODIMENTS The approach of the invention, which provides an effective protocol for recovery of heterologous recombinant proteins from microorganisms and other host cells wherein refractile inclusion bodies are formed, is presented in diagrammatic forms, including various available alternatives, as FIGS. 1 and 2 herein.

The requirement, that decitraconylation of recombinant protein antigens must precede their use in immunoassays, is demonstrated in FIG. 9. Deblocking of citraconylated recombinant HTLV-III/LAV protein antigen was necessary for its full expression of immunoreactivity, although it is clear that even citraconylated protein retains some activity in the ELISA test.

EXAMPLE 4

Latex Agglutination Test for Antibodies to the HTLV-III/LAV AIDS Virus Protein Citraconylated recombinant HTLV-III/LAV protein antigen was physically adsorbed to latex beads (2.5% suspension of 0.6 micron diameter beads) in sodium bicarbonate buffer, pH 9.0 during a 16 hour incubation with constant gentle stiring at 25° C. Citraconyl groups were then removed by treatment of adsorbed protein with 0.1M sodium acetate buffer, pH 4.0, for 16 hours at 25° C.

Antigen-coated latex beads were collected by brief centrification at low speed, then resuspended in 1% bovine serum albumin-0.06% Tween 20 in PBS buffer, pH 7.6, in order to block non-specific binding sites. The final concentration of resuspended beads was 0.6%. Coated beads were stored at 4° C.

The test for antibodies was performed by mixing 25 ul of a patient's serum with 15 ul of coated latex beads on a glass slide, then rotating the slide at 100 RPM for 8 minutes at 25° C.

A positive result for antibodies to the antigen was represented by agglutination of the coated latex beads, said agglutination being visible to the unaided eye. Alternatively, low magnification microscopy was used.

The results of 50 such tests are shown in Table II. Twenty-two of 24 sera that had been positive by the ELISA test were also positive by the latex bead agglutination (LBA) test. Retests of the two discordant samples were positive when the sera were used in undiluted form. All 24 sera that were negative by ELISA test were also negative by the LBA test. These results indicate that, at a 1:10 dilution of sera, the LBA test is 92% sensitive and 100% specific, whereas using undiluted sera the sensitivity and specificity are both 100%, relative to the ELISA test.

Having now fully described the invention it will be apparent to one with ordinary skill in the art that many changes and modifications may be made thereto without departing from the spirit or scope of the invention as set forth herein.

TABLE I

ELISA ASSAYS FOR HTLV-III/LAV ANTIBODIES IN HUMAN SERUM

| PATIENT SERA | | CONTROL SERA | |
|---|---|---|---|
| SAMPLE | ELISA READING | SAMPLE | ELISA READING |
| CDC-1 | 2.10 | CDC-30 | 0.19 |
| CDC-5 | 2.10 | WM-7 | 0.12 |
| CDC-6 | 1.92 | WM-9 | 0.11 |
| CDC-8 | 2.10 | B800 | 0.13 |
| CDC-9 | 1.98 | B805 | 0.22 |
| CDC-11 | 2.10 | F768 | 0.21 |
| CDC-13 | 2.10 | SK2-13 | 0.07 |
| CDC-18 | 2.01 | USA-12 | 0.08 |
| CDC-20 | 2.10 | 0087 | 0.23 |
| WM-6 | 1.00 | A348 | 0.18 |
| WM-10 | 0.66 | SK4-NRP | 0.19 |
| P-7 | 2.10 | 760C | 0.24 |
| P-8 | 2.10 | N1 | 0.04 |
| P-9 | 2.10 | N3 | 0.10 |
| P-10 | 2.10 | N11 | 0.07 |
| SK2-15 | 1.86 | N15 | 0.02 |
| SK2-11 | 2.10 | N73 | 0.16 |
| SK2-12 | 2.10 | N75 | 0.29 |
| SK2-17 | 0.65 | N82 | 0.07 |
| SK3-2 | 0.75 | N89 | 0.02 |
| SK3-4 | 2.10 | N126 | 0.24 |
| SK3-5 | 0.41 | PL-4 | 0.00 |
| SK3-9 | 1.27 | ORNEG | 0.01 |
| SK3-10 | 2.10 | 75-4080-0 | 0.13 |
| SK4-14 | 2.10 | HN-144 | 0.04 |

TABLE II

LATEX BEAD AGGLUTINATION TEST FOR HTLV-III/LAV ANTIBODIES IN HUMAN SERUM*

| PATIENT SERA | | CONTROL SERA | |
|---|---|---|---|
| SAMPLE | RESULT* | SAMPLE | RESULT* |
| A208004 | 2+ | 26 | NR |
| A20806 | 4+ | 27 | NR |
| A202411 | 4+ | 28 | NR |
| A206210 | 3+ | 29 | NR |
| A206110 | 3+ | 30 | NR |
| A102008 | 3+ | 31 | NR |
| A16103 | 3+ | 32 | NR |
| 003 | 4+ | 33 | NR |
| 014 | 2+ | 34 | NR |
| 017 | 1+ | 35 | NR |
| POS. CONTROL | 3+ | 36 | NR |
| RC | 4+ | 37 | NR |
| P5 | 2+ | 38 | NR |
| P7 | 3+ | 39 | NR |
| P8 | 3+ | 40 | NR |
| P9 | 4+ | 41 | NR |
| P10 | 4+ | 42 | NR |
| 6273 | 2+ | 43 | NR |
| 6316 | 3+ | 44 | NR |
| 6272 | 3+ | 45 | NR |
| 6310 | 3+ | 46 | NR |
| SK2-14 | 3+ | 48 | NR |
| SK2-17 | WR | 48 | NR |
| SK2-21 | WR | 49 | NR |

TABLE II-continued
LATEX BEAD AGGLUTINATION TEST
FOR HTLV-III/LAV ANTIBODIES IN HUMAN SERUM*

| PATIENT SERA | | CONTROL SERA | |
|---|---|---|---|
| SAMPLE | RESULT* | SAMPLE | RESULT* |
| | | 50 | NR |

*Sera diluted 1:10
NR: No reaction
+Subjective estimation by unaided eyes.
WR: Weak reaction undiluted

What is claimed as new and desired to be covered by Letters Patent are:

1. A process for recovering refractile body recombinant protein from microorganisms comprising:
   (a) disrupting host cells containing said refractile body recombinant protein;
   (b) solubilizing said refractile body recombinant protein;
   (c) acid acylating free amino groups contained in said recombinant protein;
   (d) separating said recombinant protein in N-acid acylated form; and
   (e) recovering said recombinant protein.

2. The process of claim 1 wherein sulfhydryl groups, if any, of said recombinant protein are derivatized reversibly or irreversibly prior to acid acylation of amino groups.

3. The process of claim 1 wherein said recombinant protein comprises a heterologous protein expressed in a host microorganism.

4. The process of claim 3 wherein the recombinant protein comprises viral antigens.

5. The process of claim 3 wherein the viral antigen is HTLV-I, HTLV-II, or HTLV-III/LAV antigens.

6. The process of claim 3 wherein the viral antigen consists of Feline Leukemia Virus antigens.

7. The process of claim 3 wherein the recombinant protein comprises the expression product of a eukaryotic gene in a microorganism.

8. The process of claim 3 wherein the recombinant protein comprises the expression product of a prokaryotic gene in a microorganism.

9. The process of claim 1 wherein said microorganism is bacteria, yeast, fungi, or algae.

10. The process of claim 1 wherein in step (a) said cells are disrupted utilizing disrupting agents comprising enzymes.

11. The process of claim 10 wherein said enzymes are selected from the group consisting of Lipozyme, Lysozyme, Lysing Enzyme Mixture, Mutanolysin, Lysostaphin, and DNAse.

12. The process of claim 1 wherein in said step (a) said cells are disrupted utilizing mechanical means.

13. The process of claim 1 wherein in said step (b) said solubilizing agent comprises a chemical.

14. The process of claim 13 wherein said chemical comprises a surface active agent.

15. The process of claim 13 wherein said chemical comprises a denaturing agent.

16. The process of claim 15 wherein said denaturing agent is a weak denaturing agent.

17. The process of claim 16 wherein said weak denaturing agent comprises urea.

18. The process of claim 15 wherein said denaturing agent is a strong denaturing agent.

19. The process of claim 18 wherein said strong denaturing agent comprsies guanidine.HCl.

20. The process of claim 2 wherein said sulfhydryl groups are reversibly derivatized.

21. The process of claim 20 wherein said sulfhydryl groups are reversibly derivatized by the reversible formation of disulfide bonds utilizing agents selected from the group consisting of cysteine, glutathione, o-iodosobenzoate, sodium tetrathionate, and 5,5'-dithiobis(2-nitrobenzoate).

22. The process of claim 20 wherein reversal of disulfide formation utilizes reducing agents selected from the group consisting of sodium phosphorothiolate, cysteine, dithiothreitol, 2-mercaptoethanol, and sodium borohydride.

23. The process of claim 2 wherein sulfhydryl groups are irreversibly alkylated.

24. The process of claim 23 wherein said sulfhydryl groups are irreversibly alkylated by irreversible alkylating agents selected from the group consisting of iodoacetic acid, iotoacetamide, N-ethylmaleimide, 3-bromopropionic acid, and acrylonitrile.

25. The process of claim 1 wherein in said claim (d) acid acylation comprises contacting the free amino groups of recombinant proteins with acid acylating reagents at a pH of above about 7.5.

26. The process of claim 25 wherein said acid acylating reagents are organic cyclic acid anhydrides.

27. The process of claim 26 wherein said organic cyclic acid anhydride comprises citraconic anhydride.

28. The process of claim 26 wherein said organic cyclic acid anhydride is maleic anhydride, citraconic anhydride, dimethylmaleic anhydride, exo-3,6-endoxo $\Delta^4$-tetrahydrophthalic anhydride, or exo-3,6-endoxo-$\Delta^4$-hexahydrophthalic anhydride.

29. The process of claim 1 wherein in said claim (e) said recombinant protein in N-acid acylated form is separated from other protein derivitives.

30. The process of claim 2 wherein said recombinant protein in S-derivatized and N-acylated form is separated from other protein derivatives.

31. The process of claims 29 or 30 wherein said separation comprises a chromatographic separation.

32. The process of claim 1 wherein in claim (e) recombinant protein is recovered in native form.

33. The process of claim 32 wherein sulfhydryl groups are restored to the recombinant protein.

34. The process of claim 33 wherein sulfhydryl groups are restored to the reduced state by contact with a reducing agent.

35. The process of claim 34 wherein said reducing agent is sodium phosphorothiolate, 2-mercaptoethanol, dithiothreitol, sodium borohydride or sodium sulfite.

36. The process of claim 32 wherein free amino groups are restored to the recombinant protein.

37. The process of claim 36 wherein N-acid acyl groups are removed by contact with acidic buffers of below about pH 6 at appropriate temperatures for appropriate times.

* * * * *